US006979734B1

(12) United States Patent
Paping et al.

(10) Patent No.: US 6,979,734 B1
(45) Date of Patent: Dec. 27, 2005

(54) USE OF RUBBER LATEX IN COMBINATION WITH STARCH

(75) Inventors: Max Gregor Paping, St. Michielsgestel (NL); Johannes Jeekel, Rotterdam (NL)

(73) Assignee: Budev Medical B.V., (NL)

( * ) Notice: Subject to any disclaimer, the term of this patent is extended or adjusted under 35 U.S.C. 154(b) by 0 days.

(21) Appl. No.: 10/009,348

(22) PCT Filed: May 8, 2000

(86) PCT No.: PCT/NL00/00294

§ 371 (c)(1),
(2), (4) Date: Jun. 14, 2002

(87) PCT Pub. No.: WO01/08584

PCT Pub. Date: Feb. 8, 2001

(30) Foreign Application Priority Data

May 5, 1999 (EP) .................................. 99201412
May 5, 1999 (EP) .................................. 99201413

(51) Int. Cl.[7] ........................ B29C 41/14; B29C 41/22; A41D 19/00
(52) U.S. Cl. ................... 536/124; 536/123.1; 536/128; 536/41; 536/45; 536/55.3; 536/24.3; 536/24.31; 2/168; 427/2.3; 428/36.4; 428/36.8; 428/323; 264/232
(58) Field of Search .......................... 536/41, 45, 55.3, 536/123.1, 124, 128, 126, 24.3, 24.31; 523/332; 428/323, 36.4, 368; 264/232; 2/168; 427/2.3

(56) References Cited

U.S. PATENT DOCUMENTS

| | | | |
|---|---|---|---|
| 3,617,383 A | | 11/1971 | Thurston et al. |
| 4,053,379 A | | 10/1977 | Fox et al. |
| 4,143,109 A | * | 3/1979 | Stockum ...................... 264/112 |
| 4,465,702 A | | 8/1984 | Eastman et al. |
| 4,634,596 A | | 1/1987 | Eastman |
| 5,037,929 A | | 8/1991 | Rajagopalan et al. |
| 5,057,157 A | | 10/1991 | Jane et al. |
| 5,385,608 A | * | 1/1995 | Fitt et al. .................. 106/206.1 |
| 5,563,241 A | | 10/1996 | Beezhold |
| 5,691,446 A | * | 11/1997 | Dove ....................... 525/333.7 |
| 5,777,004 A | | 7/1998 | Trautman |

OTHER PUBLICATIONS

Beezhold, D.H., *The Guthrie Journal* 61(2): 77-81 (1992).

* cited by examiner

*Primary Examiner*—James O. Wilson
*Assistant Examiner*—Devesh Khare
(74) *Attorney, Agent, or Firm*—The Webb Law Firm

(57) ABSTRACT

The present invention relates to rubber latex comprising an amount of starch, which rubber latex has a reduced allergen activity as compared to the same rubber latex without starch. In addition, the invention relates to the use of modified starch as donning powder for surgical gloves, wherein the used starch is a granular, low crystalline, preferably a non-crystalline starch.

12 Claims, 1 Drawing Sheet

USE OF RUBBER LATEX IN COMBINATION WITH STARCH

FIELD OF THE INVENTION

Figure 1:
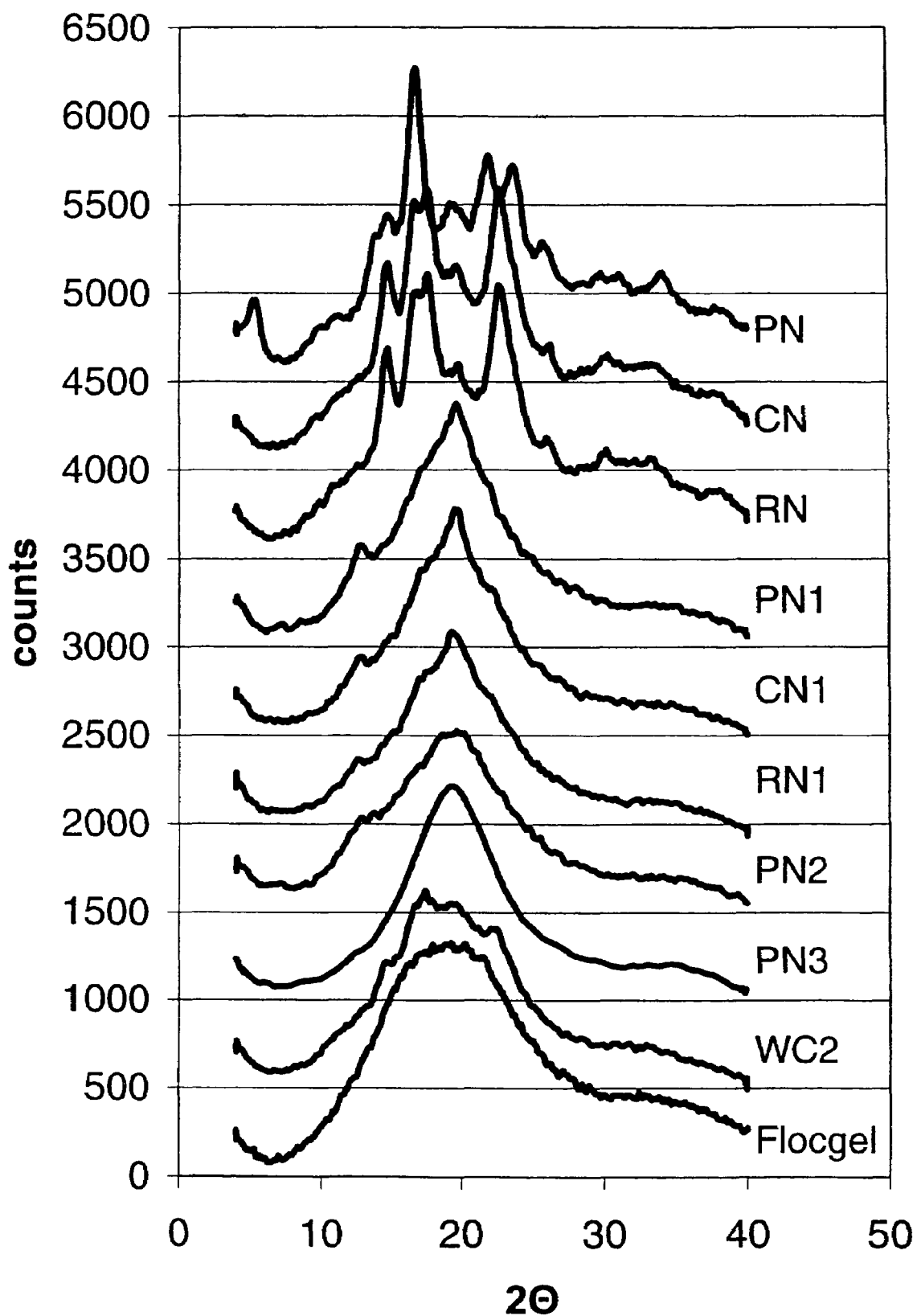

The present invention relates to the use of rubber latex in combination with starch.

BACKGROUND OF THE INVENTION

A Rubber latex is being used for the production of a variety of products, such as surgical gloves, condoms etc. The use of rubber latex has, however, been associated with several drawbacks, such as for example latex allergies in health care personnel wearing rubber latex surgical gloves. These reactions may be due to direct allergic reactions resulting from direct contact of the rubber latex allergens with the skin of the wearer, or may result from inhalation of airborne latex allergens adhered to the starch powder that is commonly used as donning powder for rubber latex surgical gloves. The starch powder itself, when used in surgery, may be left behind in the patient's wound and can, besides the aforementioned hypersensitivity reactions, also lead to the formation of granulomas and adhesions.

The present invention aims to obviate the drawbacks that are associated with the use of rubber latex articles, such as surgical gloves.

It is thus a first object of the invention to reduce the allergen activity of natural rubber latex in order to reduce the incidence of latex allergies.

It is another object of the present invention to provide a donning powder for rubber latex surgical gloves which is easily absorbed by body tissues and thus does not give rise to granuloma formation and adhesions when introduced into the body.

SUMMARY OF THE INVENTION

These objects are achieved by the present invention by the use of rubber latex in combination with starch.

DETAILED DESCRIPTION OF THE INVENTION

The present invention thus relates to rubber latex with a reduced allergen activity, to a method for preparing said rubber latex, and to medical and non-medical articles comprising said rubber latex, all in which the rubber latex is combined with starch.

Natural rubber latex is processed almost exclusively from the sap of the Hevea Brasilliensis tree (>99%), which is commonly found in Africa and Southeast Asia. Rubber workers collect the sap, a milky white dispersion known as liquid latex, by cutting deep strips into the bark of the tree. The liquid latex is an emulsion of rubber particles (cis-1, 4,-polyisoprene) with diameters ranging from 5 nm to 3 $\mu$m (<d>=0.25–0.8 $\mu$m) in an aqueous serum. The rubber particles are coated with a negatively charged layer of proteins, lipids and phospholipids that provide the structural integrity and stability of the dispersion.

For the manufacture of natural rubber products, such as latex rubber gloves, the starting material is the concentrated latex. The gloves are manufactured by dipping porcelain or glass moulds into the liquid latex. This can be achieved by dipping the moulds in a coagulating salt (calcium alginate) and then dipping them into a prevulcanized latex concentrate, yielding film thicknesses between 0.2 and 0.8 mm, or by dipping the moulds several times in the latex, and crosslinking the gloves afterwards. In the second method the films are not allowed to dry completely between dips in order to ensure homogeneous film formation. One dip accounts for approximately 0.05 mm. The final rubber product contains 93–96% polyisoprene and up to 3% protein by weight.

As a consequence of the increasing use of natural rubber articles, such as for example surgical gloves, the occurrence of latex allergy in hospital personnel and patients has become a major problem. Thus, more and more people are using surgical or examination gloves made from natural rubber latex containing a high level of proteins, which are the cause of the latex allergies. In particular, health care personnel and patients have shown a growing sensitivity to natural rubber products. The current estimate of healthcare workers being allergic to natural rubber gloves ranges between 10 and 20%. This phenomenon has been attributed to the recent dramatic rise in the use of latex gloves by medical, dental and auxiliary personnel for the protection against AIDS and hepatitis viruses. Although the allergic reactions are most obvious with respect to natural rubber gloves, a large number of other natural rubber articles are on the market, like balloons, condoms, footwear, clothing, adhesives, carpet backing etc. resulting in latex allergies as well. The problem of sensitivity to latex is therefore not restricted to (surgical) gloves.

The clinical manifestations of immediate hyper-sensitivity to latex usually arise from direct contact with natural rubber, but may also result from inhalation of airborne latex allergens. The symptoms and signs may be localized or generalized urticaria (development of wheals, flares and hives), angioedema, rhinitis, conjunctivitis, asthma, tachycardia and/or anaphylactic shock (increased heart beat rate, lowered blood pressure and possible loss of consciousness).

Allergy to latex is a typical example of an immunologically-mediated immediate hypersensitivity reaction, which is induced by allergenic proteins in the latex and is mediated by IgE antibodies. This reaction is known as a Type I allergy.

There are over 240 polypeptides in natural rubber latex, as detected by two dimensional electrophoresis. The protein concentration of a native latex sap was reported to be 16.53 mg/ml. A quarter of these proteins is associated with the rubber particles, while the rest is present in the non-rubber fractions. The number of allergenic polypeptides/proteins identified as allergens (in humans) ranges from 11 to 57.

A number of allergenic proteins have recently been detected in latex sap, ammoniated latex and extracts of rubber gloves. Thus, a trypsin-sensitive allergen was demonstrated with a molecular weight around 30 kDa. In addition, it has been found that the Rubber Elongation Factor (REF=58 kDa), which plays an important role in the polymerization of the polyisoprene chains, is a major allergen in latex. Of the major allergen prohevein (20 kDa) and the prohevein C-domain (14 kDa) it was found that its N-terminal 43-amino acid fragment hevein carries the main IgE-binding epitope. Hevein is the most predominant protein in natural rubber latex and has chitin binding properties. A 23 kDa polypeptide, which shows some amino acid sequences similar to the REF also shows allergen activity. Furthermore, lysozyme (27 kDa), which is related to the defense-related proteins in rubber latex, a 46 kDa and a 36 kDa protein are found to be allergens.

The latex proteins are believed to dissolve in the body sweat inside the gloves and are then absorbed through the skin. The onset of latex sensitization is insidious in nature and is progressive. It occurs slowly, sometimes over a period of many years, as the body is repeatedly exposed to latex and develops an immunologic memory to the proteins. The presence of latex specific IgE antibodies in the bloodstream precedes the development of clinical symptoms by months or years. It is not known what level of protein is required to actually sensitize an individual. Because of this no regulation exists for limiting the amount of allergenic protein that a product may contain.

In addition, most latex gloves are manufactured with a corn starch powder to facilitate donning. The allergenic proteins adhere to the donning powder, which may become airborne when the gloves are snapped on and off. As a result many healthcare workers inhale the protein-laden powder over a period of several years and thus may develop latex sensitivity.

Chemicals which are added to the latex prior to processing may also cause a severe rash and irritation. However, reaction to these chemicals is most commonly a Type IV allergy. Symptoms for Type IV allergy develop within 24 to 72 hours of exposure.

In order to measure the sensitivity to latex a number of allergy tests are available. The most reliable test is the skin prick test, in which a person is exposed to latex or latex extract via contact with the skin. Afterwards the reaction of the exposed skin is monitored. The latex RadioAllergoSorbent Test (RAST) is available for the in vitro detection of latex IgE antibodies (Latex, k82, Pharmacia Diagnostics), but is less sensitive than skin prick tests. In addition, a new latex-specific fluorescent enzyme immunoassay for the detection of latex specific IgE antibodies has been brought on the market (Pharmacia CAP System, PCS).

The in vitro assays show considerable variation in the total protein and allergen content of different glove brands. Furthermore, the amount of protein eluting from a glove depends on the method used and does not always correlate with the allergenicity in skin prick tests, indicating that the total protein measurement is not a sufficient method to monitor the allergenic properties of latex gloves.

In an attempt to reduce the allergenic effect of the allergens in gloves, the gloves are run through a chlorine wash process, known as leaching, after they are dipped and dried, to remove the proteins which are responsible for the allergic reactions. However, in efforts to speed up production and meet increasing demands, glove manufacturers may fail to adequately wash the gloves. Steam sterilization of the gloves further decreases the protein level.

The activity of allergens in latex can also be reduced by treatment with an alkaline potassium hydroxide solution. However, to reduce the allergenic effect of the latex an extra step in the production process is needed. In addition, the gloves will be more costly.

Another option is the use of latex-free gloves. These gloves can be made of neoprene, styrene butadiene block copolymer or styrene ethylene butadiene styrene block copolymer. However, these non-latex gloves often have inferior barrier properties and often are found to lack the comfort and fit of natural rubber latex gloves. Furthermore, they are less environmental-friendly as the energy required to produce them is 7–11 times more than is the case of natural rubber and they are generally not biodegradable. In addition, except for vinyl, the synthetic gloves are more costly.

Alternative methods to remove or inactivate the allergens in the latex are described in U.S. Pat. No. 5,563,241 in which the rubber latex is contacted with an anion exchange resin. Subsequently, the protein-resin complex is removed from the latex. U.S. Pat. No. 5,691,446 relates to a method of dipping the dried rubber product in a chemical substance that inactivates the allergens on the surface. Again, extra steps are needed for the manufacturing of latex articles. In U.S. Pat. No. 5,777,004 proteases are added to the liquid latex for denaturation of the allergenic proteins. These proteases, however, may be the cause of allergic reactions themselves.

As a result of the high incidence of latex allergies the use of latex articles, such as surgical gloves, has been restricted or even banned from hospital environments, indicating the significance and impact of the problem of latex allergies.

In the research that led to the present invention the effect of incorporating starch in rubber latex was investigated. It has thus been shown that by incorporating a small amount of starch in the rubber latex the allergen activity of said rubber latex can be reduced. The starch can form both physical and chemical bonds with the amino and acid groups of the proteins, thus binding potentially allergenic proteins.

Sources for the starch as used in the invention are starch preparations, which generally comprise starch and a small amount of other constituents, such as proteins. According to the present invention, preferably low-protein, colloidal starches are used.

According to the invention, the "allergen activity" of rubber latex refers to the amount of water-soluble allergens in extracts made from said rubber latex. Thus, in order to measure the allergen activity of rubber latex, extracts are made from rubber latex samples (as described in Example 1) and the amount of water soluble-allergens in these extracts is determined using a Latex Elisa for Antigenic Proteins (LEAP) test (Beezhold, The Guthrie Journal 61, 77–81, 1992). It has been shown that by adding small amounts of starch the allergen activity of the latex rubber samples (i.e. the amount of water-soluble allergens in a rubber latex extract) is significantly decreased as compared to the same rubber latex without starch, thus resulting in a reduced incidence of allergic reactions in persons contacting said rubber latex.

Comfort tests have shown that the use of starch concentrations of less than 10 w % do not have a negative effect on the mechanical properties of the samples. When more starch is added, the rubber samples are too stiff in order to be used in rubber articles, such as gloves.

According to a preferred embodiment of the present invention, the rubber latex comprises an amount of starch for reducing the allergen activity of rubber latex such that the allergen activity of said rubber latex is maximally 50%, preferably maximally 40%, more preferably maximally 30%, most preferably maximally 25% of the allergen activity of rubber latex without starch, as measured by a latex ELISA for antigenic proteins.

In particular, according to the present invention the rubber latex preferably comprises an amount of starch for reducing the allergen activity of rubber latex such that the allergen activity of said rubber latex is maximally 20%, preferably maximally 15%, more preferably maximally 10%, most preferably maximally 5% of the allergen activity of rubber latex without starch, as measured by a latex ELISA for antigenic proteins. The allergen activity of the rubber latex according to the invention thus is significantly reduced as compared to the currently used rubber latex without starch.

Preferably, the used starch is a modified starch. Methods for obtaining modified starch are for example described by Wurzburg (in: Modified starches: Properties and Uses, 19.86; CRC Press Inc, Eds, Bocaraton, Florida, USA). However, according to the invention modified starch is preferably obtained by gelatinizing the starch in an extruder, and crosslinking the starch with glyoxal as described in the co-pending European patent application No. 99200203.0 and Example 1 of the present application. Particles of the modified starch (100–200 nm) are dispersed in water to obtain a 10 w % dispersion, which is then mixed with liquid rubber latex.

According to the present invention various starches can be used, such as for example potato starch, Tapioca, waxy corn starch and waxy rice starch.

The invention further relates to a method for reducing the allergen activity of rubber latex comprising incorporating an amount of starch in the rubber latex. In particular, the invention relates to a method for reducing the allergen activity comprising incorporating an amount of starch in the rubber latex such that the allergen activity of said rubber latex is maximally 50%, preferably maximally 40%, more preferably maximally 30%, most preferably maximally 25% of the allergen activity of rubber latex without starch, as measured by a latex ELISA for antigenic proteins.

According to a particularly preferred embodiment of the invention the method for reducing the allergen activity of rubber latex comprises incorporating an amount of starch in the rubber latex such that the allergen activity of said rubber latex is maximally 20%, preferably maximally 15%, more preferably maximally 10%, most preferably maximally 5% of the allergen activity of rubber latex without starch, as measured by a latex ELISA for antigenic proteins.

The fact that the method according to the invention involves low material costs and can be easily implemented in the existing glove manufacturing processes, without significant investments, is an important advantage of the present invention.

Furthermore, the invention relates to rubber latex articles, such as surgical gloves, condoms, inflatable balloons etc., comprising the rubber latex of the invention, wherein at least the surface contacting the skin of the user is fabricated from the modified rubber latex.

The invention further relates to the use of starch for reducing the allergen activity of rubber latex, and to the use of the rubber latex according to the invention for the manufacture of rubber latex articles.

By using the rubber latex of the present invention for the manufacture of rubber latex articles the incidence of allergic reactions to latex can be significantly reduced. This is particularly important for health care personnel, such as dental, medical and auxiliary personnel, as they are at the highest risk for developing severe latex allergies.

The present invention further relates to the use of a modified starch as donning powder for surgical gloves, and to a surgical glove provided with said modified starch as donning powder.

In the process of making surgical or examination gloves a mould of glass or ceramic is dipped in a concentrate of liquid natural rubber latex. After drying, the resulting rubber product remains a little sticky. In order to reduce this stickiness generally a starch powder is applied to the gloves after manufacturing.

Starch (mostly corn starch), which absorbs humidity, thus is the main constituent of glove powder. When used in surgery, it is possible that some of this corn starch powder is left behind in the patient's wound. This would not be a problem if the starch were completely absorbed by the body. However, it has been shown that residual starch can lead to the formation of granulomas and adhesions. These granulomas are caused by foreign particles which cannot be broken down in the body and form adhesions. When the damaged tissue is investigated with an optical microscope with crossed polarisers a Maltese cross is observed, typical for the presence of starch granules.

To prevent the formation of starch powder granulomas after operation it is known to remove all traces of the starch powder from the glove. However, in order to obtain totally powder free gloves the gloves have to be rinsed intensively with chemical compounds, which is both time-consuming and expensive.

It is also known to use non-powdered gloves in order to reduce the incidence of starch granulomas and adhesions. Several non-powdered gloves are on the market, and the lubrication of these gloves is obtained by a variety of methods, ranging from hydrogels to multilayer systems. However, these non-powdered gloves are far more expensive (about 3 times) than the powdered ones. In addition, non-powdered gloves are thicker and thus less comfortable to wear than powdered gloves. They are more slippery, more difficult to don (the hands must be totally dry) and have a worse grip on the instruments. According to the present invention it has been found that by the decrease of crystallinity of the modified starch according to the invention granuloma and adhesion formation due to starch contamination of body tissues can be reduced.

Initially, surgical gloves were sterilized by means of autoclaving. The replacement of this technique by gamma sterilization resulted in a dramatic increase of case reports of starch granulomas. It has been shown that autoclaved starch was almost completely absorbed from the peritoneal cavity of a rat within a period of 48 h, whereas irradiated starch was still not fully absorbed after 70 days. Scanning electron microscopy indicated that autoclaved starch showed pitting and cracking of the granule surface, while irradiated starch showed a smooth surface. It was therefore concluded that autoclaving damaged the starch in such a way that rapid absorption occurs.

Native starch is normally deposited in roots, tubers, grains etc, as semi-crystalline granules. It is known from the literature that the amorphous (non-crystalline) parts of the starch granules are easily attacked by the amylase enzymes which are present in saliva and blood. In contrast, the crystalline parts of the granule, which are more ordered and dense, are not very sensitive to enzymatic attack. For this reason, the semi-crystalline starch granules, if introduced in the human or animal body, are likewise not sensitive to enzymes, and are therefore not easily absorbed by the body tissues.

In the research that led to the present invention it has been found that in order to be suitable as donning powder for rubber gloves, the starch powder should have a suitable particle size (<50 $\mu$m). Starch having larger particles, like thermoplastic starch pellets, should be ground which will increase the price of the powder. In addition, the low- or non-crystalline starch should be spherical or oval shaped in order to preserve the lubrication properties. This means that the best shape is the granular form of unmodified starch.

According to a preferred embodiment of the present invention, the modified starch thus is a granular, low crystalline, preferably non-crystalline, starch. The granular, low-crystalline modified starch preferably has a so-called V-type crystal structure.

Methods for reducing the crystallinity of starch are known, based on the gelatinisation of starch with water or glycerol at elevated temperatures, or by increasing the pH by using NaOH. Such methods for the preparation of granular non-crystalline starch are for example described in U.S. Pat. No. 3,617,383, U.S. Pat. No. 4,465,702, and U.S. Pat. No. 4,634,596, which relate to a method for the preparation of cold water swelling starches. This method is based on mixing the granular, crystalline starch with water and a non-solvent for the starch, such as methanol or ethanol, and heating the slurry to temperatures between 140 and 180° C. at elevated pressures. An alternative method has been described in U.S. Pat. No. 5,037,929 wherein the alcohol is substituted by a polyhydric alcohol, like propanediol or glycerol. The temperature can thus be reduced to 100–120° C. and an atmospheric pressure can be applied. In U.S. Pat. No. 5,057,157 granular cold water swelling starch is obtained by alcoholic/alkali treatments at ambient temperatures and pressures. These procedures result in the formation of V-type crystals or to an amorphous starch structure. The application of modified starch as a donning powder for rubber gloves has, however, not been described before.

In the research that led to the present invention five different types of starch were modified using a heat and/or alkali treatment in order to reduce the crystallinity in the granules. Two of the used modification methods were already described in the literature. In a third method only water and a sodium hydroxide solution was used. These methods are further described in Example 2.

The modified starches were characterized by optical microscopy with crossed polarizers for the measurement of birefringence (indicating the presence or absence of crystallinity). In addition, the amount and type of crystallinity was determined by X-ray diffraction. It was found that all three modification methods reduced the crystallinity, or even completely eliminated the crystalline structure of the starch granules.

According to a preferred embodiment of the present invention the birefringence of the modified starch is less than 30%, preferably less than 20%, more preferably less than 10%, and most preferably less than 5% of native starch.

Furthermore, it has been found that the starch powder should not be completely soluble in cold water, because this would cause the gloves to become too sticky and reduce the wearing comfort. For these reasons, the use of thermoplastic starch or lower molecular carbohydrates like maltodextrines is eliminated. According to a preferred embodiment of the invention preferably less than 75% of the modified starch is soluble in cold water.

Preferably, the modified starch according to the present invention is derived from native potato starch, native corn starch, native rice starch, or waxy corn starch.

The modified starch of the present invention is preferably used as a donning powder for rubber latex gloves, so called surgical gloves. Such gloves may however also be used for various other medical and non-medical applications.

The invention further relates to a surgical glove provided with modified starch as a donning powder at least on the surface of the glove to be contacting the skin of the user. To provide a surgical glove with the modified starch, different known methods of powdering the gloves may be used.

The invention will further be illustrated by the following examples and figure.

In FIG. 1 the results of the X-ray diffraction measurements of the modified starches are visualized.

EXAMPLES

Example 1

Preparation of the Rubber Latex of the Invention

A concentrated natural rubber latex was delivered in a drum with a total solid content of approximately 62%, which was modified by the incorporation of a modified strach as allergen-reducing compound.

The starch was a modified native potato starch. An extruder was used to gelatinise and crosslink the starch with glyoxal. A mixture of potato starch and glycerol (87:13) was fed into a twin screw extruder. After gelatinisation, a crosslinker (1–4 w % glyoxal) was injected and the starch was crosslinked. The extrudate thus obtained was dried, ground and dispersed in water, resulting in a 10% dispersion of starch particles (100–200 nm). The liquid latex was mixed with the starch dispersion. The weight fraction of the starch in the dried sample ranged from 0–30%. Fractions of 1–2% gave however the best results.

After the compounds were mixed, test tubes were dipped in the latex for the production of latex specimens. The number of dips ranged between one and four, and the drying temperature was 50° C. After preparation, the dried rubber samples were powdered with native cornstarch in order to reduce the stickiness of the rubber.

Sample Characterization

As described earlier, natural rubber latex specimens were made by dipping test tubes in the liquid rubber latex of the invention. This resulted in condom shaped rubber samples (samples: NR00S, NR01S, NR02S).

Since the addition of starch may modify the mechanical properties of the rubber, it was investigated whether the elasticity and strength of the modified rubber was changed after the incorporation of the starch. In addition, both total protein content and allergen content of the samples were determined.

The total amount of soluble proteins was measured using turbidity measurements. A 10% (w/v) extract was made from small pieces cut from the rubber samples in a phosphate buffer with 0.03% HSA and 0.5% phenol. After one hour of shaking, the extracts were centrifuged for 10 min. at 2000 g. The supernatant was filtered over a Millipore 0.22 $\mu$m filter. The extracts were stored at –22° C. A small amount of the extract was preincubated in an alkaline solution containing EDTA. Benzethonium chloride (Boehringer Mannheim U/CSF) was then added, producing a turbidity which was read at 505 nm.

The amount of water-soluble allergenic proteins in the rubber latex extracts was determined using the Latex ELISA for Antigenic Proteins (LEAP) as used in the Allergology department of the Academic Hospital of Rotterdam (Beezhold, The Guthrie Journal 61, 77–81, 1992).

Results

Wearing Comfort:

The comfort tests showed that after addition of starch to the rubber latex, the elasticity of the dipped samples was reduced. This increment of the stiffness was most notable for samples having a starch content higher than 10%. The elasticity modulus of the 10% starch-latex samples was three times higher than that of the non-modified ones. Furthermore, the surface of the samples became less smooth with increasing starch load. From this it was concluded that the mechanical properties of the samples having a starch load up to 10% were comparable to the non-modified samples.

Protein Content:

In table 1 the results of the addition of 1 and 2% of modified potato starch are shown. From this table it can be concluded that the total amount of soluble proteins did not depend on the amount of starch added. This seems strange, since a dilution effect should be expected. However, the majority of measured proteins originate from the 0.03% HSA in the phosphate buffer. Furthermore, it is known that the starch preparation which is used itself also contains a small amount of proteins. In addition, it is also not inconceivable that the starch absorbs proteins in the liquid latex and thus induces an enhanced protein content in the final samples.

TABLE 1

Results of the comfort, protein and allergen tests on the modified natural rubber samples

| sample | starch w % | dips | weight (g) | comfort | protein (g/l) | allergen (µg/ml) |
|---|---|---|---|---|---|---|
| NR00S1 | 0 | 1 | 0.54 | + | 0.31 | 1.77 |
| NR00S_2 | 0 | 2 | 0.74 | + | 0.32 | 2.15 |
| NR00S_3 | 0 | 3 | 1.02 | + | 0.33 | 1.42 |
| NR01S_1 | 1 | 1 | 0.26 | + | 0.32 | 0.66 |
| NR01S_2 | 1 | 2 | 0.69 | + | 0.34 | 0.77 |
| NR01S_3 | 1 | 3 | 0.90 | + | 0.33 | 0.44 |
| NR02_1 | 2 | 1 | 0.32 | + | 0.32 | 0.38 |
| NR02_2 | 2 | 2 | 0.60 | + | 0.33 | 0.74 |
| NR02_3 | 2 | 3 | 0.95 | + | 0.32 | 4.31 |
| Romed Baxter | | | | | | >5.4 |
| Nu Tex Biogel | | | | | | |
| Comform | | | | | | |

Allergen Activity:

The most significant results of the sample characterisation are listed in the last column of table 1. In this column the allergen concentrations in µg per ml extract are given. The numbers >5.4 indicate that the allergen content is too high to be measured accurately using the method described earlier.

When the 1% and 2% starch samples were compared to the 0% sample, a decrease in the amount of water-soluble allergens of 60–75% was observed. This indicates that the addition of small amounts of starch to the liquid rubber latex before processing reduced the allergen activity of the rubber latex of the invention to maximally 25% to 40% of the allergen activity of rubber latex without starch. The allergens are absorbed at the surface of the starch particles which are subsequently fixed in the rubber matrix, resulting in a decrease of the allergen activity of natural rubber latex.

In the last row of table 1, the results of five different brands of glove are listed. The allergen content of all five brands exceeds 5.4 µg/ml extract. This means that even the 0% starch sample gave better results than the commercial brands. This may be due to the industrial processing of the gloves. The samples as described in this example were dried at 50° C. It is possible that this drying step already partly denaturises the allergenic proteins.

Example 2

Preparation of Modified Starch Powder

The starch preparations which were used were native potato starch (PN), native corn starch (CN) and native rice starch (RN). Native means that the starches have not undergone any modification prior to use. One waxy starch was used, viz. waxy corn (WC). This starch contains a high amount of amylopectin (>99%) and hardly any amylose. A pregelatinised starch (flocgel) was also incorporated in the measurements. This starch was ground after modification in order to obtain small particles possibly suitable for glove powdering.

As solvents water, glycerol and denaturated ethanol were used. A 1M solution of sodium hydroxide in water was used to increase the pH and provoke gelatinisation of some of the starches.

Three different methods for the preparation of the modified starch were used:

1. In a first method 10 g starch was added to a mixture of 38.8 g glycerol and 11.6 g water in an Erlenmeyer flask. The Erlenmeyer flask was put into a paraffin bath and heated to 130–140° C. The mixture was homogenised by a magnetic stirrer. After about 5 min, the viscosity of the slurry increased, at which time the Erlenmeyer was retrieved from the paraffin bath and cooled down to 100° C. and about 100 ml of ethanol or of an ethanol/glycerol (1:4) mixture was added. The slurry was stirred until a homogeneous mixture was obtained. This mixture was suction filtered, after which the solid mass was redispersed in ethanol in order to remove the water. This was repeated. The powder thus obtained was dried at 50° C. This method has been described in U.S. Pat. No. 5,037,929.

2. In a second method the same amounts of glycerol and starch were mixed with 10 g 1M NaOH solution. The paraffin bath was set on 120° C., which resulted in a temperature of the slurry of 100° C. After 5 min, the slurry became more viscous and the Erlenmeyer flask was removed from the heat source. Hydrochloric acid was added in order to neutralise the mixture. The viscous paste was washed with 100 ml of ethanol or ethanol/glycerol (1:4) and suction filtered. Subsequently, the powder was washed twice with ethanol and dried at 50° C.

3. In the third method 50 g of water was mixed with 5 g starch in an Erlenmeyer flask. A 1M NaOH solution was added slowly into the mixture to ensure an overall concentration of 0.2M NaOH (=13 g 1M NaOH). After the viscosity had increased, 100 ml ethanol was added to the slurry. This mixture was stirred and homogenised, and hydrochloric acid was added to neutralise the mixture. The powder obtained after suction filtration was immersed twice in ethanol and dried at 50° C.

The powder which was obtained by these methods was sieved over a 90 µm sieve.

Characterization of the Modified Starch Powder

The powders were characterised by their behaviour in cold water and examined under an optical microscope with crossed polarisers (Zeiss Axioplan). Furthermore, the amount and type of crystallinity was determined using X-ray diffraction (Philips PW3710).

The soluble fraction of the powder was obtained by mixing 0.1 g of modified starch with 5 g of cold water in a small polystyrene container. The mixture was stirred and put aside at room temperature for 24 hours, and stirred every hour for the first 5 hours. After 24 hours a layer of gelled and unmodified particles sedimented on the bottom of the container. This layer was separated from the clear liquid above, dried in a vacuum oven at 50° C. and weighed.

Since all the granulomas formed after starch contamination of body tissue showed a Maltese cross, the modified powder was also subjected to a birefringence test. The amount of particles which still showed birefringence, even after modification, was determined using an optical microscope. The modified starch was immersed in water and put between crossed polarisers. The unchanged particles showed a yellow and blue cross, whereas of the modified particles only the contours were visible. The absence of the Maltese crosses indicated a loss of original crystallinity.

X-ray diffraction was used in order to obtain information about the amount and type of residual crystallinity. Radiation from a Cu K-α source was reflected by the sample and detected by a detector, moving from $2\theta=4°$ to $2\theta=40°$. The various types of crystal structures were distinguished by their peak positions. The double helical amylopectin structures are indicated by A, B and C crystallinity, and the single helical amylose by V crystals.

Specimens of non-crosslinked natural rubber were dusted with the modified starch in order to determine whether the powder is applicable as a glove lubricant or not. The dusted rubber was tested for comfort and lubricity. The surface was wetted with cold water and tested for stickiness. Powder, which becomes very sticky is not very suitable as a lubricant.

The results of the sample preparation and material characterisation are listed in table 2. From this table, it can be concluded that the degree of solubility and amount of residual birefringence (birefr.) depends on the modification method used. The highest fraction of starch soluble in cold water is derived by a treatment with a high concentration of NaOH. The source of starch does not play a very important role. However, the waxy type, having a high amylopectin fraction, is less sensitive to the modification. The waxy starch was used in order to prevent recrystallisation of the amylose after gelatinisation of the original starch granules.

TABLE 2

| Starch[a] | Method | solv.[b] | solubility % | Birefr. % | Cryst. type[c] | comfort[d] wet behaviour |
|---|---|---|---|---|---|---|
| PN | — | — | 0 | 100 | B | +, N |
| CN | — | — | 0 | 100 | A | +, N |
| RN | — | — | 0 | 100 | A | +, N |
| PN1 | 1 | eth. | 45–50 | 5–10 | V | +/−, S |
| CN1 | 1 | eth. | 35–40 | 5–10 | V | +, N |
| RN1 | 1 | eth. | 35–40 | 1–5 | V | +, N |
| PN2 | 2 | eth. | 40–45 | 5–10 | V/Am | +, S |
| PN3 | 3 | eth. | 75–80 | 1–5 | Am | +, S |
| WC2 | 2 | eth./glyc. | 60–65 | 20–30 | A/Am | +, N |
| Flocgel | — | — | 100 | 0 | Am | −, V |

[a]PN: Native potato; CN: Native corn; RN: Native rice; WC: Waxy corn; high amylopectin content; Flocgel: Gelatinised and ground starch;
[b]Eth: Ethanol, Glyc: Glycerol
[c]Am: Amorphous;
[d]N: Not sticky; S: Slightly sticky; V: Very sticky; +: Good comfort; +/−: Reasonable comfort; −: Bad comfort.

In FIG. 1 the results from the X-ray measurements are shown. In this figure, the different curves are vertically shifted 500 counts. It can be seen that the crystallinity of the native starch sources (PN, CN, RN) is high and can be divided into an A and B type crystallinity. The potato, corn and rice starches, modified according to method 1 (PN1, CN1, RN1) all gave a similar X-ray pattern, viz. V-type crystallinity. This is indicated by the peaks at $2\theta \approx 14$ and $20°$. The two potato starches treated with NaOH (PN2 and PN3) showed a very low crystallinity. The diffraction pattern for an amorphous starch structure was visible for PN3 (obtained by method 3). Flocgel showed an amorphous X-ray pattern indicating the absence of residual crystallinity. Finally, the crystallinity of the waxy starch was reduced considerably. It was clear that no V-type crystallinity was formed, since the peaks at $2\theta \approx 14$ and 200 were absent.

The behaviour of the powder when applied to the sticky surface of non-crosslinked natural rubber was diverse. The granular starches reduced the stickiness of the gloves. The results of the potato starch were slightly less smooth, due to the larger granule size. Dusting the rubber surface with Flocgel did not result in a smooth surface, because the particles obtained by grinding the gelatinised starch were too coarse.

After wetting the dusted surfaces the stickiness was again tested. The Flocgel became very sticky, because the powder dissolved almost completely in cold water. The modified potato starches (PN1, PN2 and PN3) showed a slight stickiness. The waxy starch and corn and rice starch did not show an enhanced stickiness. Comparing these findings to the results of the solubility measurements, it is obvious that the amount of soluble material in the dusting powder has a large influence on the wet behaviour. The solubility, and thus the stickiness, can be reduced by crosslinking the powder before or after modification. In this way the soluble chains are incorporated in the granules.

What is claimed is:

1. A method for reducing the allergen activity of rubber latex for use in a rubber latex article, comprising incorporating starch into the liquid rubber latex before forming the article.

2. The method according to claim 1, wherein the allergen activity of said rubber latex is maximally 50% of the allergen activity of rubber latex without starch, as measured by a latex ELISA for antigenic proteins.

3. The method according to claim 1, wherein the allergen activity of said rubber latex is maximally 20% of the allergen activity of rubber latex without starch, as measured by a latex ELISA for antigenic proteins.

4. The method according to claim 1, wherein the starch is a modified starch, and wherein the allergen activity of said rubber latex is maximally 40%.

5. The method according to claim 4, wherein the modified starch is obtainable by gelatinizing the starch in an extruder and subsequently crosslinking the starch with glyoxal, and wherein the allergen activity of said rubber latex is maximally 15%.

6. The method according to claim 1, wherein the starch is selected from the group consisting of potato starch, Tapioca, waxy corn starch, waxy rice starch and mixtures thereof, and wherein the allergen activity of said rubber latex is maximally 5%.

7. The method according to claim 1, wherein the amount of starch is maximally 10 wt. %.

8. A rubber latex article comprising rubber latex having a reduced allergen activity, comprising an amount of starch that is homogeneously distributed throughout the rubber latex, wherein said amount is maximally 10 wt. %, and wherein the allergen activity of said rubber latex is maximally 50% of the allergen activity of rubber latex without starch, as measured by a latex ELISA for antigenic proteins.

9. The rubber latex article comprising rubber latex according to claim 8, wherein at least the surface contacting the skin of the user is fabricated from the said rubber latex.

10. The rubber latex article according to claim 9, wherein the article is a surgical glove.

11. The rubber latex article according to claim 9, wherein the article is a condom.

12. The rubber latex article according to claim 9, wherein the article is an inflatable balloon.

* * * * *